United States Patent
Lerner (10) Patent No.: US 10,422,777 B1
(45) Date of Patent: Sep. 24, 2019

(54) CLAMP FOR CHROMATOGRAPHY COLUMNS

(71) Applicant: BIO-RAD LABORATORIES, INC., Hercules, CA (US)

(72) Inventor: David Lerner, Corte Madera, CA (US)

(73) Assignee: BIO-RAD LABORATORIES, INC., Hercules, CA (US)

(*) Notice: Subject to any disclaimer, the term of this patent is extended or adjusted under 35 U.S.C. 154(b) by 0 days.

(21) Appl. No.: 15/858,871

(22) Filed: Dec. 29, 2017

(51) Int. Cl.
*G01N 30/60* (2006.01)
*G01N 30/46* (2006.01)

(52) U.S. Cl.
CPC ..... *G01N 30/6047* (2013.01); *G01N 30/6034* (2013.01); *G01N 30/6039* (2013.01); *G01N 30/461* (2013.01)

(58) Field of Classification Search
CPC .................. G01N 30/6047; G01N 30/6034
See application file for complete search history.

(56) References Cited

U.S. PATENT DOCUMENTS

| 4,655,917 A * | 4/1987 | Shackelford ........... B01D 15/22 210/198.2 |
| 9,983,178 B2 * | 5/2018 | Michienzi .......... G01N 30/6052 |
| 2007/0084982 A1 * | 4/2007 | Martone ............ G01N 30/6047 248/316.8 |
| 2015/0209787 A1 * | 7/2015 | Brann .................. G01N 30/461 29/469 |
| 2015/0323509 A1 * | 11/2015 | Kirby ..................... G01N 30/30 210/175 |
| 2017/0322189 A1 | 11/2017 | Brandlhuber |

FOREIGN PATENT DOCUMENTS

| EP | 3 242 131 | 11/2017 |
| WO | 2005/087339 | 9/2005 |
| WO | 2013/095964 A2 | 6/2013 |

OTHER PUBLICATIONS

PCT International Search Report and Written Opinion from PCT/US2018/067974 dated Apr. 15, 2019.

* cited by examiner

*Primary Examiner* — Francis C Gray
(74) *Attorney, Agent, or Firm* — Ladas & Parry, LLP (57) ABSTRACT

A clamp for chromatography columns has a first seal with a first opening a movable seal with a second opening and a movable coupler. The movable coupler has first and second coupler seals with communicating third and fourth openings. The clamp is arranged for pressing a first chromatography column between the first seal and the first coupler seal and for pressing a second chromatography column between the movable seal and the second coupler seal, such that the first opening fluidly communicates with the second opening through the first chromatography column, the third and fourth openings and the second chromatography column.

20 Claims, 6 Drawing Sheets

CLAMP FOR CHROMATOGRAPHY COLUMNS

TECHNICAL FIELD

This presentation relates to a method and corresponding apparatus for coupling in series two chromatography columns.

BACKGROUND

Chromatography techniques such as liquid chromatography, gas chromatography, low pressure chromatography, medium pressure chromatography, high-performance liquid chromatography (HPLC), ultra-high performance chromatography (UHPLC), etc. can be used, for example, in an analytical role or in a preparative role to separate, identify, and quantify the components of a mixture. Such techniques essentially pass a fluid ("mobile phase") containing a sample mixture through a column containing a separation medium ("stationary phase.") The stationary phase and mobile phase can be chosen such that components in the sample have different affinity for the stationary and mobile phase, causing different flow rates for the different components and leading to the separation of the components as they flow through the column. The stationary phase can be a granular material comprising, for example, a ceramic or a polymeric material, selected for the particular separation being performed.

It is desirable for a chromatography system to be arranged to quickly, easily and reliably couple two chromatography columns in a chromatography system.

SUMMARY

Embodiments of this presentation provide for a clamp for chromatography columns, that has a first seal, for example a non-movable seal, with a first opening a movable seal with a second opening and a movable coupler. The movable coupler has first and second coupler seals with communicating third and fourth openings. The clamp is arranged for pressing a first chromatography column between the first seal and the first coupler seal and for pressing a second chromatography column between the movable seal and the second coupler seal, such that the first opening fluidly communicates with the second opening through the first chromatography column, the third and fourth openings and the second chromatography column.

In a first aspect disclosed herein a clamp for chromatography columns is provided, the clamp having a first seal with a first opening, a movable seal with a second opening and a movable coupler; the movable coupler having first and second coupler seals with communicating third and fourth openings; the clamp being configured for pressing a first chromatography column between the first seal and the first coupler seal and pressing a second chromatography column between the movable seal and the second coupler seal, such that the first opening fluidly communicates with the second opening through the first chromatography column, the third and fourth openings and the second chromatography column.

In a second aspect disclosed herein a chromatography column clamp is provided, the chromatography claim is arranged: to receive two chromatography columns between a first compression seal and a movable compression seal; and to press said two chromatography columns on opposite sides of a compression seal coupler by urging the movable compression seal toward the first compression seal.

In a third aspect disclosed herein, a method of clamping two chromatography columns in series is provided, the method comprising: receiving two chromatography columns between a first compression seal and a movable compression seal; and pressing said two chromatography columns on opposite sides of a compression seal coupler by urging the movable compression seal toward the first compression seal.

These and other features and advantages will become further apparent from the detailed description and accompanying figures that follow. In the figures and description, numerals indicate the various features; like numerals referring to like features throughout both the drawings and the description.

DETAILED DESCRIPTION

In the following description, numerous specific details are set forth to clearly describe various specific embodiments disclosed herein. One skilled in the art, however, will understand that the present disclosure may be practiced without all of the specific details discussed below. In other instances, well known features have not been described so as not to obscure the understanding of the disclosure. In the present disclosure, the same references indicate the same elements in the various figures.

Chromatography can be used for separating components for manufacturing purpose, as well as for analysis purpose (detecting if specific products are present in a solution).

Chromatography can be categorized based on the pressure used to pass the mobile phase through the stationary phase. For example, HPLC utilizes a higher pressure than medium pressure chromatography, which utilizes a higher pressure than low pressure chromatography with utilizes a higher pressure than flash chromatography. In some forms of chromatography, gravity or a liquid column can be used as the pressure source.

A chromatography system can include a detector arranged to generate a signal related to the amount of sample component emerging from the column, thus allowing for quantification of the sample components. HPLC instruments can have a column heater that allows for adjusting the temperature at which the separation is performed.

A chromatography system can fluidly couple a first chromatography column, such as one that serves as a prefilter or fluid conditioner, upstream of a second chromatography column which contains a stationary phase, for example to filter out large particles from the sample that would otherwise impair the flow of the sample through the stationary phase, or to otherwise condition the mobile phase or the sample. In some embodiments, a chromatography column can have threaded end connections. However, due to the possibility of over-tightening or under-tightening, leaks and/or alignment issues can arise during operation. Further, properly tightening a threaded connection can require special tools and additional time to accomplish, both adding to the burden put on the user.

An embodiment of this presentation relates to a clamp arranged to fluidly couple two chromatography columns, such as by pressing two chromatography columns on opposite sides of a compression seal coupler. The two chromatography columns can be pressed between a first (for example a non-moving) compression seal and a movable, pressure applying, compression seal. As used herein, "chromatography column" can be used to refer to a column that contains the stationary phase that can provide separation of sample components and can be used to refer to other chromatography system components such as a "pre-column", "guard column", filter, pre-filter, post-filter as well as component(s) that react with one or more components of the mobile phase or sample, such as to remove, neutralize, modify or change the detectability of a component. Frequently, these other chromatography system components can be arranged in series with the chromatography column that contains the stationary phase. In some embodiments, two or more chromatography columns that contain stationary phase (either the same or different from one another) are also contemplated.

Figure 1:
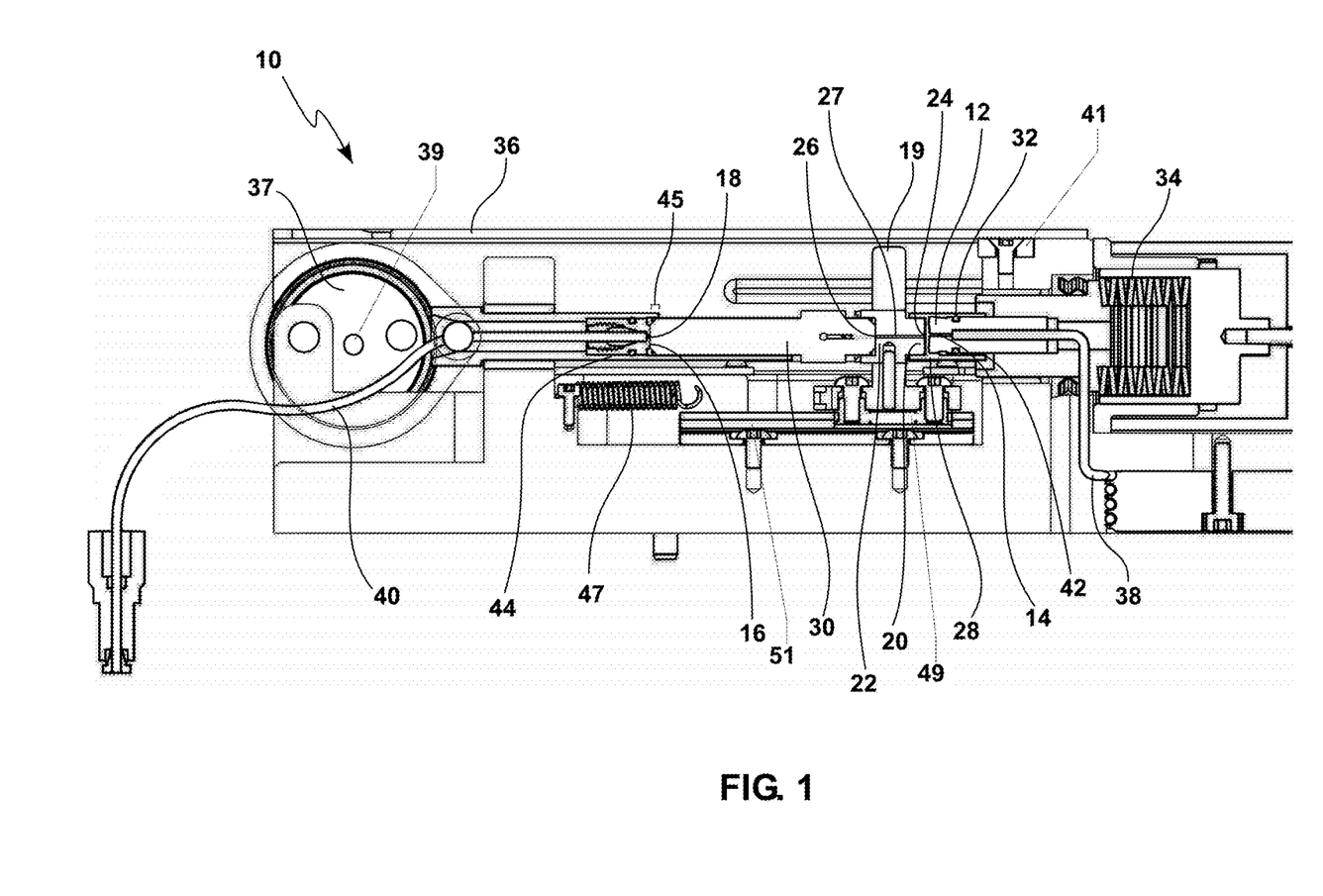
FIG. 1 is a cross-section view of a clamp for chromatography columns according to an embodiment of this presentation, in a work position.

FIG. 1 is a cross-section view of a clamp for chromatography columns 10 according to an embodiment of this presentation, the clamp 10 having on one side a first, for example non-movable, seal 12 with a first opening 14; and on another side a movable seal 16 with a second opening 18. Between the two sides, claim 10 comprises a movable coupler 19 that comprises a first coupler seal 20 with a third opening 24 and a second coupler seal 22 with a fourth opening 26. The third and fourth openings 24, 26 can fluidly communicate via a lumen 27. By "non-movable" in reference to a seal, means that no specific mechanism is provided to actively change the position of the first seal 12 in operation of the clamp 10. As detailed herein, in some embodiments the position of the first seal 12 can be tuned/calibrated to account for a change of length of the chromatography columns or to vary the compressive force. As detailed herein, the position of the first seal 12 as a non-moving seal can in some embodiments vary its position in response to the pressure exerted by movable seal 16 through the chromatography columns 28, 30 and the mobile coupler 19.

According to an embodiment of this presentation, and as detailed hereafter, clamp 10 can be arranged for pressing a first chromatography column 28 (for example a filter column, a pre-column, a guard column or a stationary phase column) between the first seal 12 and the first coupler seal 20 and for pressing a second chromatography column 30 (for example a column containing stationary phase) between the movable seal 16 and the second coupler seal 22, in a manner such that the first opening 14 fluidly communicates with the second opening 18 through the first chromatography column 28, the third and fourth openings 24, 26 (through lumen 27) and the second chromatography column 30. According to an embodiment of this presentation, the first seal 12, the first coupler seal 20, the movable seal 16 and the second coupler seal 22 are all compression seals.

It is noted that in the Description above the first chromatography column 28 is described as a filter column, a pre-column, a guard column or a stationary phase column and the second chromatography column 30 is a containing stationary phase, but that the first chromatography column 28 could be a column containing stationary phase with the second chromatography column 30 being a filter column, a pre-column, a guard column or a stationary phase column, or that both columns could be stationary phase columns.

According to an embodiment of this presentation, the movable seal 16 can be arranged to move between a rest position (illustrated and described hereafter in FIGS. 2-6), where it is possible to remove, install or replace one or both of the chromatography columns 28, 30 in the clamp, and a work position (illustrated in FIG. 1), where the clamp presses the first chromatography column 28 between the first seal 12 and the first coupler seal 20 and presses the second chromatography column 30 between the movable seal 16 and the second coupler seal 22.

According to an embodiment of this presentation, the first opening 14, the first chromatography column 28, the third opening 24, the fourth opening 26, the second chromatography column 30 and the second opening 18 can be coaxially aligned when in the work position.

According to an embodiment of this presentation, a lever 36 can be configured for actuating the movable seal 16 between the rest and work positions. As illustrated in FIG. 1, lever 36 can be coupled to movable seal 16 via a cam mechanism 37 that transforms a rotation of lever 36 around an axis perpendicular to the clamp axis 39 into a translation of movable seal 16 along the clamp axis. It is to be noted that, due to axis 39 being referenced to cam mechanism 37, axis 39 is not fixed but moves for example along an arc of a circle as lever 36 rotates around axis 39.

According to an embodiment of this presentation, lever 36 can form a cover preventing access to the first and second chromatography columns 28, 30 in the work position, as illustrated in FIG. 1, and allowing access to the first and second chromatography columns in the rest position, as illustrated in FIGS. 2-6.

According to an embodiment of this presentation, cam mechanism 37 can be arranged such that a reduced release force is exerted by the clamp on the lever at the beginning of a motion of lever 36 away from its work position; a larger release force being exerted by the clamp on the lever later along the motion of lever 36, for example when the lever 36 is moved a predetermined angle away from its work position. The predetermined angle can be comprised between 5 and 15 degrees, but other angles can be successfully used. The predetermined angle can be of 10 degrees. According to an embodiment of this presentation, a magnet 41 can be arranged to retain lever 36 in the work position.

According to an embodiment of this presentation, the movable seal 16 can be arranged in a first section of a tube 44; a side portion (top side in FIG. 1) of the tube 44 being removed from the end of the tube proximal the first seal 12 to a location proximal the movable seal 16 so that the tube 44 forms an open ended trough capable of receiving the second chromatography column 30. According to an embodiment of this presentation, a full diameter of tube 44 can be kept intact along a length 45 between the movable seal 16 and the beginning of the trough to allow maintaining radial alignment of the second chromatography column 30 against the movable seal 16. In additional embodiments, different shapes can be used for the tube 44 and open ended trough, such as a tube shape having 3, 4, 5, 6, 7, 8 or more sides, and the trough can be flat or comprise a number of flat surfaces. In some embodiments, the trough can be absent. In some embodiments, the tube 44 can fit inside the second chromatography column 30 or can fit around chromatography column 30.

According to an embodiment of this presentation, the first seal 12 can be arranged to resiliently exert pressure (or force) on the first chromatography column 28, the first coupler seal 20 and the coupler 19 and optionally to the second coupler seal 22, the second chromatography column 30 and the movable seal 16 when the clamp is in the work position. In some embodiments, the pressure exerted by the first seal 12 can be a controlled pressure. In some embodiments, the controlled pressure can be achieved by axially mounting first seal 12 on a spring 34 or other resilient feature. The spring 34 or other resilient feature can exert a force directly or indirectly to the first seal 12. In some embodiments, the spring 34 can be configured to apply an adjustable force to the first seal 12 or to controllably change the force resiliently exerted by the first seal 12. According to an embodiment of this presentation, the first and second chromatography columns 28, 30 can have first and second lengths comprised in first and second lengths ranges. In some embodiments, spring 34 can be actuated to change the pressure resiliently exerted by the first seal 12 if the length or length range of the chromatography columns is changed. In some embodiments, spring 34 can comprise or be a Belleville spring or a coil spring or a wave spring or a leaf spring or a torsion spring or another type of spring. In some embodiments, spring 34 can comprise or be a resilient material, either solid or porous. In some embodiments, one or more of the coupler seals and in particular the first and second coupler seals 20, 22 can have axial resiliency, either due to the material they are made from or to a resilient mounting (not shown).

According to an embodiment of this presentation, clamp 10 can comprise a first retainer 32 for retaining the first chromatography column in contact with the first seal 12. In some embodiments of a first retainer, the first retainer 32 can interconnectively interact with an end of the first chromatography column. In some such embodiments, the first retainer 32 can comprise a male portion optionally fitted with a frictional element arranged to frictionally cooperate with an inside diameter of a lumen 42 in the first chromatography column 28. According to an embodiment of this presentation, the frictional element 32 can comprise an o-ring, as illustrated in FIG. 1. In some embodiments, the first retainer 32 can comprise a female portion optionally fitted with a frictional element. In some embodiments, the interaction between the first retainer 32 and the first chromatography column can be through a third part.

According to an embodiment of this presentation, clamp 10 can comprise a spring 47 for urging the movable coupler 19 toward the movable seal 16. Movable coupler 19 thus can operate in some embodiments as a second retainer 19 that retains the second chromatography column 30 in contact with the movable seal 16. According to an embodiment of this presentation, clamp 10 can be arranged such that in the rest position (described hereafter) movable coupler 19 is not in contact with the first chromatography column 28, which can then be put in contact with (or removed from) the first seal 12 without moving the movable coupler 19; and such that the second chromatography column 30 can be arranged in contact with (or removed from) the movable seal 16 after moving the movable coupler away from the movable seal 16 to release the second chromatography column 30 from the movable coupler 19. According to embodiments of this presentation, movable coupler 19 can be coupled to a carriage 49 arranged to slide axially along a rail 51 fixedly attached to the clamp 10.

In some embodiments of this presentation, spring 47 can be replaced by gravity. In some embodiments of this presentation, for example if spring 47 is not present and movable coupler 19 is not urged toward movable seal 16, clamp 10 can utilize another retainer to retain the second chromatography column 30 to the movable seal 16 in addition to or instead of the retaining function provided by movable coupler 19. In some embodiments, such another retainer can comprise attachment(s) for attaching the second chromatography column 30 to the seal or to tube 44 or the trough in tube 44.

According to an embodiment of this presentation, the first and second openings of clamp 10 can be respectively coupled to a fluid input pipe 38 and to a fluid output pipe 40; the fluid output pipe 40 can be sufficiently flexible for flexing without damage when movable seal 16 is actuated between the rest and work positions. According to an embodiment of this presentation, fluid input pipe 38 can be placed in thermal communication with a heater or cooler 39, such as by winding the fluid input pipe around a heater or cooler 39 provided for controlling the temperature of the fluid sent into the first chromatography column. In some embodiments one or more of the fluid output pipe 40 and fluid input pipe 38 can be a metallic tube or a plastic tube. Suitable materials for the fluid output pipe 40 and/or the fluid input pipe can be selected from among materials such as corrosion resistant metals (e.g. stainless steels, nickel, nickel alloys, titanium, titanium alloys, etc., the composition and grades of such metals can be found on the websites and publications of manufacturers of metals, tubing and chromatography systems and are incorporated by reference herein) and plastics (e.g. PEEK, PTFE, PE, PP, PEEKsil, etc. the composition and grades of such plastics can be found on the websites and publications of manufacturers of plastics, tubing and chromatography systems and are incorporated by reference herein.)

Figure 2:
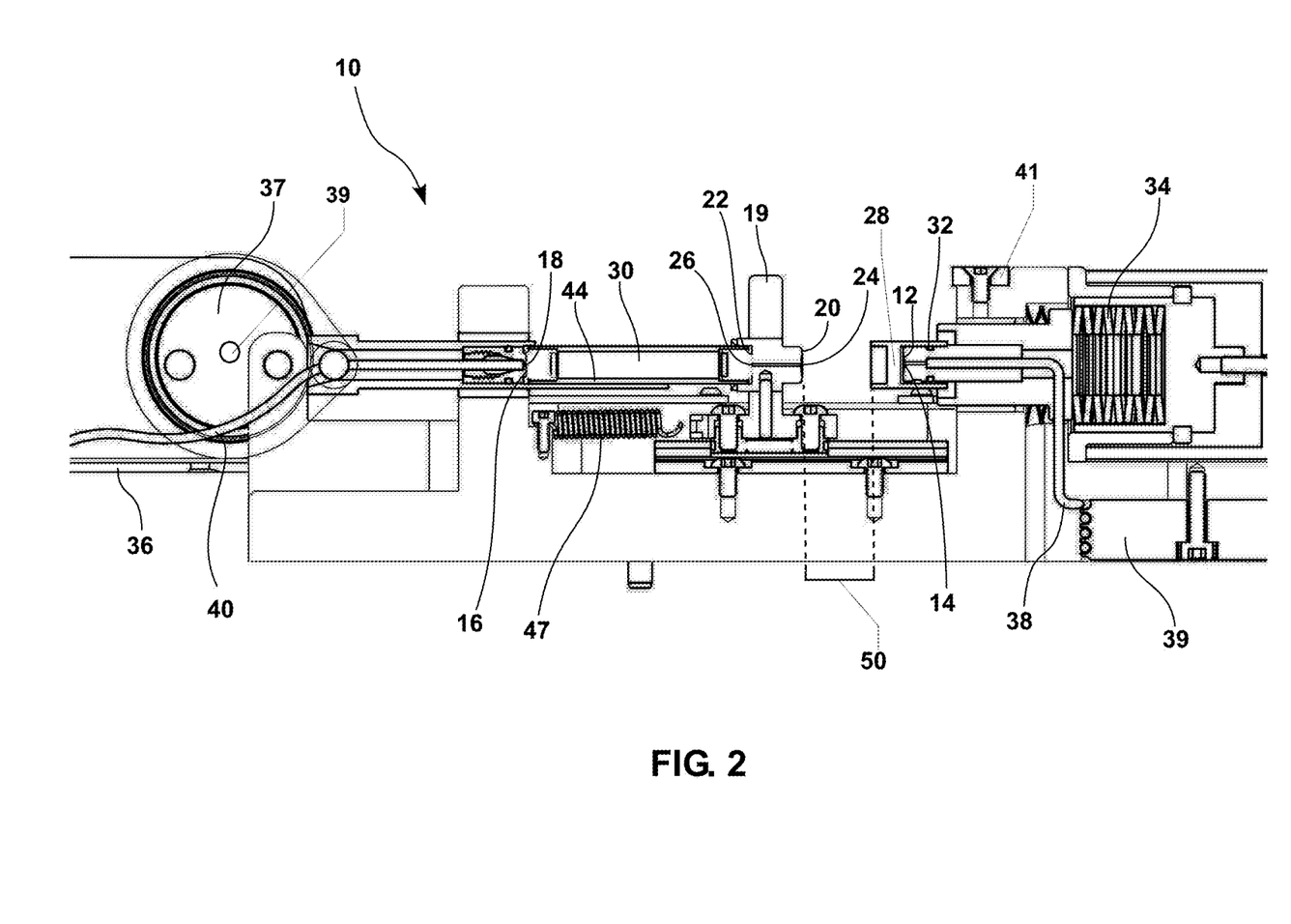
FIG. 2 is a cross-section view of a clamp for chromatography columns according to an embodiment of this presentation, in a rest position.

FIG. 2 shows an embodiment of clamp 10 of FIG. 1 in the rest position and shows lever 36 rotated into the open position (e.g. away from the first and second chromatography columns 28, 30.) According to an embodiment of this presentation, rotating the lever 36 into the open/rest position (e.g. away from the first and second chromatography columns 28, 30) can cause cam mechanism 37 to axially move movable seal 16 away from first seal 12. In some embodiments, such as some embodiments where a spring 47 urges movable coupler 19 toward movable seal 16, moving movable seal 16 away from first seal 12 also moves movable coupler 19 away from the first chromatography column 28 and first seal 12. This allows access to first chromatography column 28, and allows installing, removing and replacing first chromatography column 28, such as by disengagement of the first chromatography column 28 from the first seal 12 and movement of the first chromatography column 28 away from clamp 10 to remove the first chromatography column 28, and reversing this procedure to install the first chromatography column 28. In some embodiments, the first chromatography column can be removed by movement of the first chromatography column along its longitudinal axis followed by movement of the first chromatography column away from the clamp 10 to remove the first chromatography column 28, and reversing this procedure to install the first chromatography column 28.

According to an embodiment of this presentation, in the rest position movable coupler 19 can be spaced apart from first chromatography column 28 by a distance 50 that is sufficient to allow a user to free the second chromatography column 30 from movable coupler 19 by moving (e.g. manually) movable coupler 19 toward first chromatography column 28. Thus, a user can install, remove and replace the second chromatography column 30 in the rest position.

Figure 3:
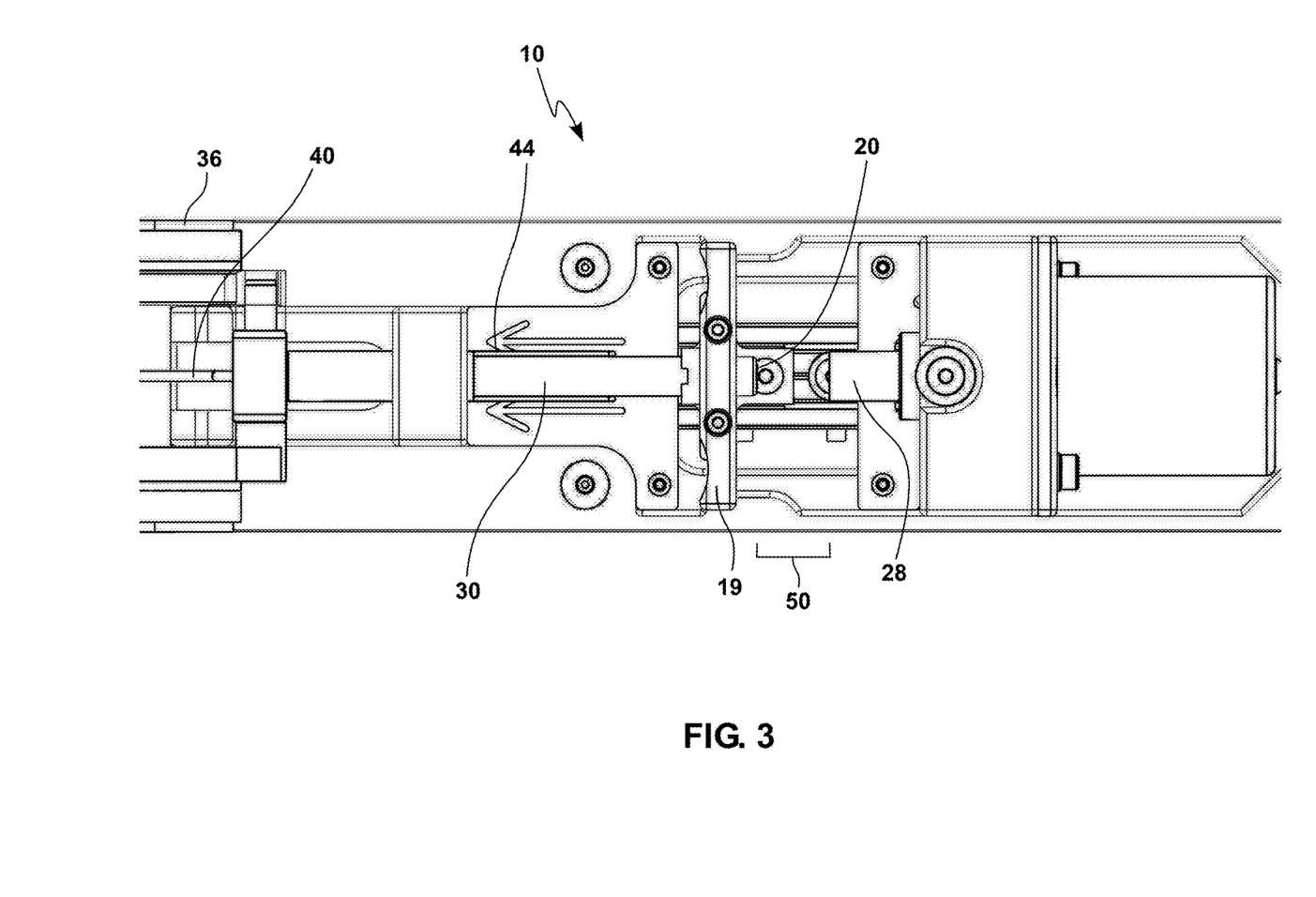
FIG. 3 is a top view of a clamp for chromatography columns according to an embodiment of this presentation, in a rest position.

FIG. 3 is a top view of clamp 10 in the rest position, showing the second chromatography column 30, maintained on trough tube 44 and in contact with the movable seal 16 (not shown) by movable coupler 19; the first coupler seal 20 of movable coupler 19 being at a distance 50 away from first chromatography column 28.

Figure 4:
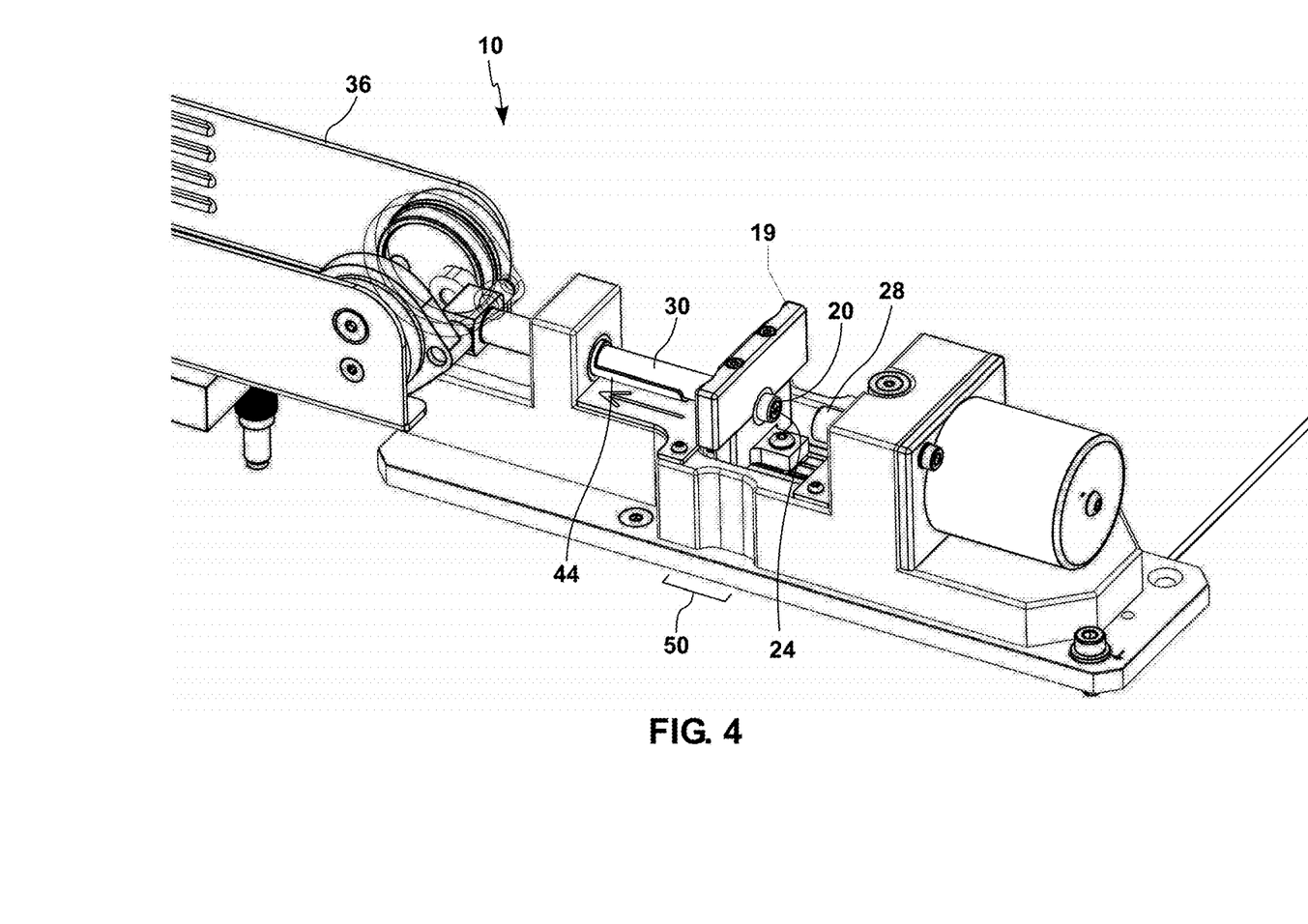
FIG. 4 is an elevation view of a clamp for chromatography columns according to an embodiment of this presentation, in a rest position.

FIG. 4 is an elevation view of clamp 10 in the rest position, showing the second chromatography column 30, maintained on trough tube 44 and in contact with the movable seal 16 (not shown) by movable coupler 19; the first coupler seal 20 of movable coupler 19 being at a distance 50 away from first chromatography column 28.

Figure 5:
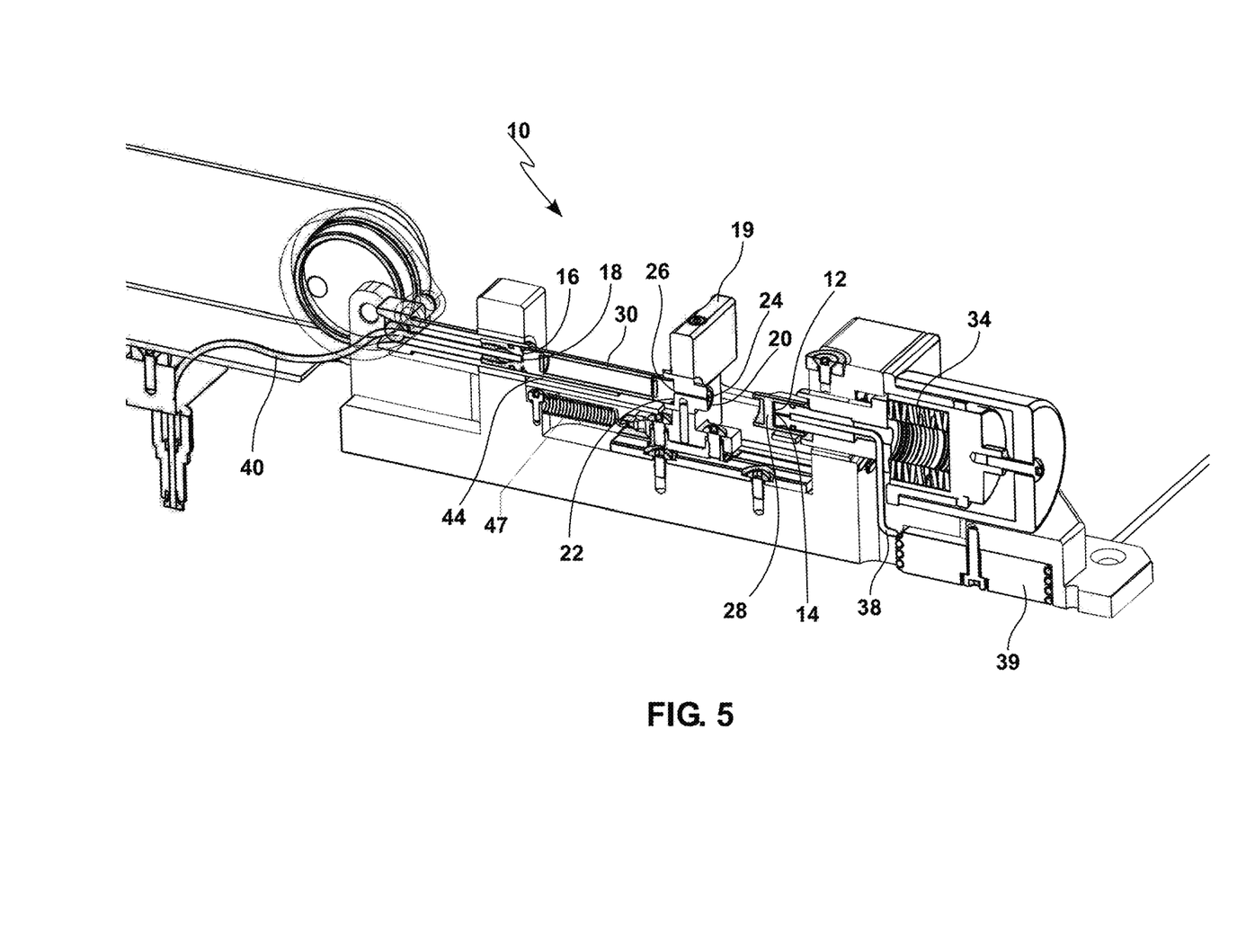
FIG. 5 is a cut-away view of the clamp for chromatography columns shown in FIG. 4.

FIG. 5 is a cut-away view of the clamp for chromatography columns shown in FIG. 4, showing the elements described in particular in relation with FIGS. 1 and 2.

In some embodiments, a portion of the second chromatography column 30 can be accessible to the first chromatography column 28 through the mobile coupler 19, so as to allow a direct fluid communication between the first chromatography column 28 and the second chromatography column 30. In some embodiments, a portion of the second chromatography column 30 can extend through the mobile coupler 19, where the first chromatography column 28 can connect to the second chromatography column 30. In some embodiments, the end of the second chromatography column 30 that connects with the first chromatography column 28 can be located within mobile coupler 19 and the end of the first chromatography column 28 can enter the mobile coupler 19 to connect with the second chromatography column 30. In some embodiments, the mobile coupler 19 can interact with an outer surface of the second chromatography column 30 at the end or be spaced back from the end of the second chromatography column 30 (e.g., wall, step, pin, extension, indentation, notch, etc.) such that the mobile coupler 19 provides a force urging the second chromatography column toward the movable seal 16.

Figure 6:
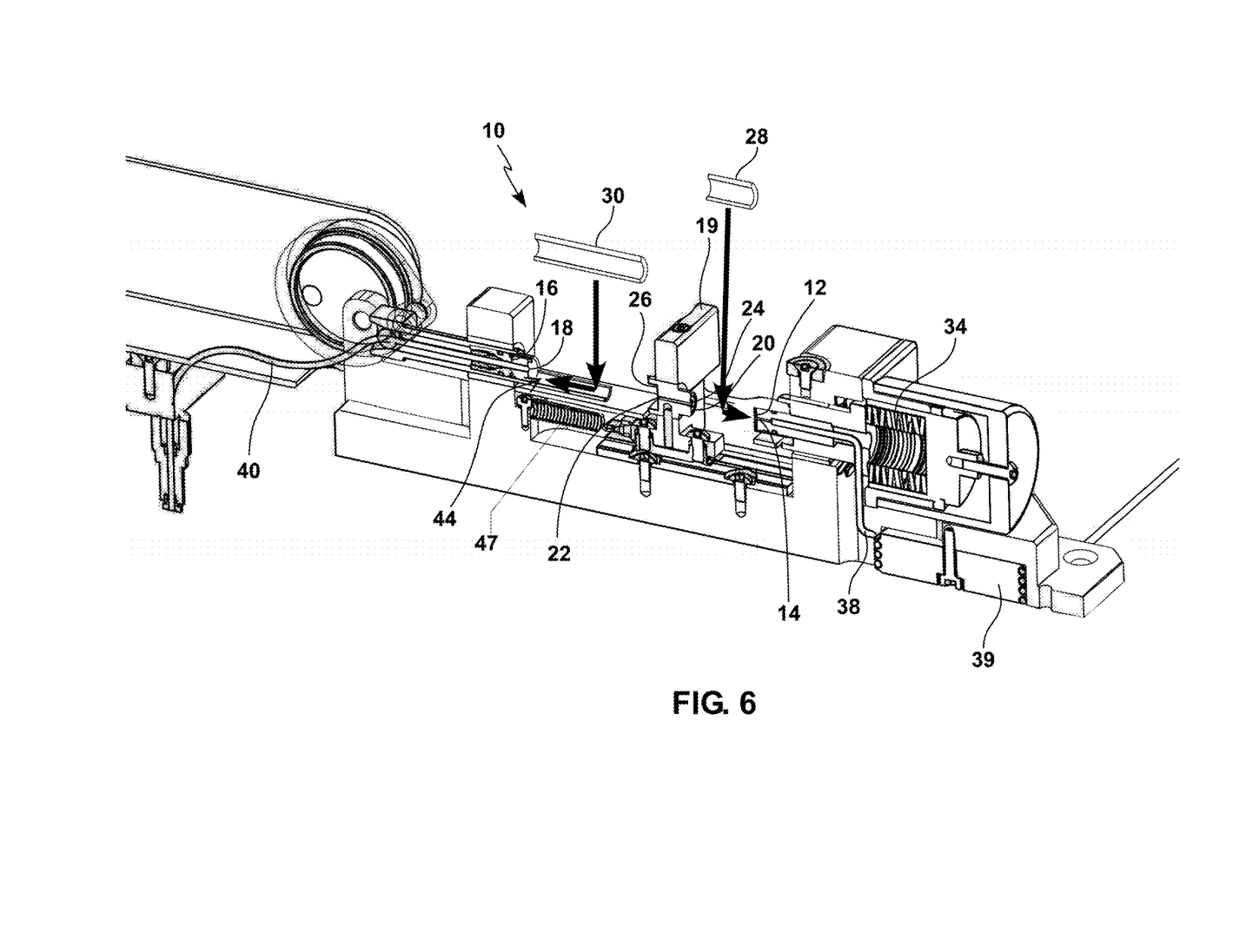
FIG. 6 is a cut-away view of the clamp for chromatography columns shown in FIG. 4, with the first and second chromatography columns removed, and showing installation.

FIG. 6 is identical to FIG. 5, but with the first and second chromatography columns removed for ease of understanding.

The foregoing has been described in connection with various embodiments, features or elements from one embodiment may be combined with other embodiments without departing from the teachings of this disclosure. Further, the combinations of features between the respective embodiments are not necessarily limited thereto. Various embodiments of the disclosure have been described. These and other embodiments are within the scope of the disclosure. In addition, those skilled in this art will understand how to make further changes and modifications to the embodiments to meet their specific requirements or conditions. Such changes and modifications may be made without departing from the scope and spirit of the present disclosure.

The foregoing Detailed Description of exemplary and preferred embodiments is presented for purposes of illustration and disclosure. It is not intended to be exhaustive nor to limit what can be claimed to the precise form(s) described, but only to enable others skilled in the art to understand how the disclosure may be suited for a particular use or implementation. The possibility of modifications and variations will be apparent to practitioners skilled in the art. For example, in the description the claim comprises a single mobile coupler 19 that couples in series first and second chromatography columns 28, 30, but one skilled in the art can easily modify the clamp to comprise one or more additional mobile couplers 19 to couple in series one or more additional chromatography columns. In such an occurrence, each additional mobile coupler 19 could be attached by a spring to a previous mobile coupler 19 so as to retain each additional chromatography column.

No limitation is intended by the description of exemplary embodiments which may have included tolerances, feature dimensions, specific operating conditions, engineering specifications, or the like, and which may vary between implementations or with changes to the state of the art, and no limitation should be implied therefrom. Applicant has made this presentation with respect to the current state of the art, but also contemplates advancements and that adaptations in the future may take into consideration of those advancements, namely in accordance with the then current state of the art and also encompasses equivalents as applicable. Reference to a claim element in the singular is not intended to mean "one and only one" unless explicitly so stated. Moreover, no element, component, nor method or process step in this presentation is intended to be dedicated to the public regardless of whether the element, component, or step is explicitly recited in the Claims.

Concepts

Concept 1. A clamp for chromatography columns, the clamp having a first seal with a first opening, a movable seal with a second opening and a movable coupler; the movable coupler having first and second coupler seals with communicating third and fourth openings;

the clamp being configured for pressing a first chromatography column between the first seal and the first coupler seal and pressing a second chromatography column between the movable seal and the second coupler seal, such that the first opening fluidly communicates with the second opening through the first chromatography column, the third and fourth openings and the second chromatography column.

Concept 2. The clamp of Concept 1, further comprising a first retainer for retaining the first chromatography column in contact with the first seal.

Concept 3. The clamp of Concept 1 or 2, wherein the movable coupler retains the second chromatography column in contact with the movable seal when the first chromatography column is not pressed against the first coupler seal.

Concept 4. The clamp of Concept 3, further comprising a spring for urging the movable coupler toward the movable seal, whereby the movable coupler maintains the second chromatography column against the movable seal.

Concept 5. The clamp of any one of Concept 1-4, wherein the first opening, the first chromatography column, the third opening, the fourth opening, the second chromatography column and the second opening are coaxially aligned when the clamp presses the first chromatography column between the first seal and the first coupler seal and presses the second chromatography column between the movable seal and the second coupler seal.

Concept 6. The clamp of any one of Concept 1-5, wherein said movable seal is configured to move between:

a rest position, where the first chromatography column is positionable in contact with the first seal and the second chromatography column is positionable in contact with the movable seal; and a work position, where the clamp presses the first chromatography column between the first seal and the first coupler seal and presses the second chromatography column between the movable seal and the second coupler seal.

Concept 7. The clamp of Concept 6, wherein the first seal is configured to resiliently exert pressure on the first chromatography column, the first coupler seal, the coupler, the second coupler seal, the second chromatography column and the movable seal in the clamp work position.

Concept 8. The clamp of Concept 7, wherein the first seal is mounted on a spring having a controlled tension, configured to controllably change the pressure resiliently exerted by the first seal.

Concept 9. The clamp of any one of Concept 6-8, further comprising a spring for urging the movable coupler toward the movable seal; the clamp being configured such that in the rest position the first chromatography column can be arranged in contact with, or removed from, the first seal without moving the movable coupler and the second chromatography column can be arranged in contact with, or removed from, the movable seal after moving the movable coupler away from the movable seal.

Concept 10. The clamp of any one of Concept 1-9, wherein said first and second chromatography columns have first and second lengths comprised in first and second lengths ranges.

Concept 11. The clamp of any one of Concept 6-9, further comprising a lever for actuating the movable seal between the rest and work positions.

Concept 12. The clamp of Concept 11, wherein the lever forms a cover preventing access to the first and second chromatography columns in the work position and allowing access to the first and second chromatography columns in the rest position.

Concept 13. The clamp of any one of Concept 1-12, wherein the first and second openings are respectively coupled to a fluid input pipe and to a fluid output pipe.

Concept 14. The clamp of Concept 2, wherein the first retainer comprises a male portion fitted with a frictional element configured to frictionally cooperate with an inside diameter of a lumen in the first chromatography column.

Concept 15. The clamp of Concept 14, wherein the frictional element comprises an o-ring.

Concept 16. The clamp of any one of Concept 1-15, wherein the movable seal is located at a first end of a tube; a side portion of said tube being removed from the end of the tube closest to the first seal to about the movable seal so that the tube forms an open ended trough capable of receiving the second chromatography columns.

Concept 17. The clamp of any one of Concept 1-16, wherein the first seal is non-movable.

Concept 18. A chromatography column clamp arranged:
to receive two chromatography columns between a first compression seal and a movable compression seal; and
to press said two chromatography columns on opposite sides of a compression seal coupler by urging the movable compression seal toward the first compression seal.

Concept 19. The chromatography column clamp of Concept 18, wherein:
the first seal has a first opening;
the movable seal has a second opening;
the movable coupler has first and second coupler seals with communicating third and fourth openings;
the clamp being configured such that the first opening fluidly communicates with the second opening through the first chromatography column, the third and fourth openings and the second chromatography column when the clamp presses the two chromatography columns on opposite sides of the compression seal coupler.

Concept 20. The chromatography column clamp of Concept 19, further comprising a spring for urging the movable coupler toward the movable seal.

Concept 21. A method of clamping two chromatography columns in series, the method comprising:
receiving two chromatography columns between a first compression seal and a movable compression seal; and
pressing said two chromatography columns on opposite sides of a compression seal coupler by urging the movable compression seal toward the first compression seal.

What is claimed is:

1. A clamp for chromatography columns, the clamp having a first seal with a first opening, a movable seal with a second opening and a movable coupler; the movable coupler having first and second coupler seals with communicating third and fourth openings;
the clamp being configured for pressing a first chromatography column between the first seal and the first coupler seal and pressing a second chromatography column between the movable seal and the second coupler seal, such that the first opening fluidly communicates with the second opening through the first chromatography column, the third and fourth openings and the second chromatography column; and
a first retainer for retaining the first chromatography column in contact with the first seal.

2. The clamp of claim 1, wherein the movable coupler retains the second chromatography column in contact with the movable seal when the first chromatography column is not pressed against the first coupler seal.

3. The clamp of claim 2, further comprising a spring for urging the movable coupler toward the movable seal, whereby the movable coupler maintains the second chromatography column against the movable seal.

4. The clamp of claim 1, wherein the first opening, the first chromatography column, the third opening, the fourth opening, the second chromatography column and the second opening are coaxially aligned when the clamp presses the first chromatography column between the first seal and the first coupler seal and presses the second chromatography column between the movable seal and the second coupler seal.

5. The clamp of claim 1, wherein said movable seal is configured to move between:
a rest position, where the first chromatography column is positionable in contact with the first seal and the second chromatography column is positionable in contact with the movable seal; and
a work position, where the clamp presses the first chromatography column between the first seal and the first coupler seal and presses the second chromatography column between the movable seal and the second coupler seal.

6. The clamp of claim 5, wherein the first seal is configured to resiliently exert pressure on the first chromatography column, the first coupler seal, the coupler, the second coupler seal, the second chromatography column and the movable seal in the clamp work position.

7. The clamp of claim 6, wherein the first seal is mounted on a spring having a controlled tension, configured to controllably change the pressure resiliently exerted by the first seal.

8. The clamp of claim 5, further comprising a spring for urging the movable coupler toward the movable seal; the clamp being configured such that in the rest position the first chromatography column can be arranged in contact with, or removed from, the first seal without moving the movable coupler and the second chromatography column can be arranged in contact with, or removed from, the movable seal after moving the movable coupler away from the movable seal.

9. The clamp of claim 1, wherein said first and second chromatography columns have first and second lengths comprised in first and second lengths ranges.

10. The clamp of claim 5, further comprising a lever for actuating the movable seal between the rest and work positions.

11. The clamp of claim 10, wherein the lever forms a cover preventing access to the first and second chromatography columns in the work position and allowing access to the first and second chromatography columns in the rest position.

12. The clamp of claim 1, wherein the first and second openings are respectively coupled to a fluid input pipe and to a fluid output pipe.

13. The clamp of claim 1, wherein the first retainer comprises a male portion fitted with a frictional element configured to frictionally cooperate with an inside diameter of a lumen in the first chromatography column.

14. The clamp of claim 13, wherein the frictional element comprises an o-ring.

15. The clamp of claim 1, wherein the movable seal is located at a first end of a tube; a side portion of said tube being removed from the end of the tube closest to the first seal to about the movable seal so that the tube forms an open ended trough capable of receiving the second chromatography columns.

16. The clamp of claim 1, wherein the first seal is non-movable.

17. A chromatography column clamp arranged:
to receive two chromatography columns between a first compression seal and a movable compression seal; and
to press said two chromatography columns on opposite sides of a compression seal coupler by urging the movable compression seal toward the first compression seal.

18. The chromatography column clamp of claim 17, wherein:
the first seal has a first opening;
the movable seal has a second opening;
the movable coupler has first and second coupler seals with communicating third and fourth openings;
the clamp being configured such that the first opening fluidly communicates with the second opening through the first chromatography column, the third and fourth openings and the second chromatography column when the clamp presses the two chromatography columns on opposite sides of the compression seal coupler.

19. The chromatography column clamp of claim 18, further comprising a spring for urging the movable coupler toward the movable seal.

20. A method of clamping two chromatography columns in series, the method comprising:
receiving two chromatography columns between a first compression seal and a movable compression seal; and
pressing said two chromatography columns on opposite sides of a compression seal coupler by urging the movable compression seal toward the first compression seal.

* * * * *

UNITED STATES PATENT AND TRADEMARK OFFICE
CERTIFICATE OF CORRECTION

PATENT NO. : 10,422,777 B1
APPLICATION NO. : 15/858871
DATED : September 24, 2019
INVENTOR(S) : David Lerner It is certified that error appears in the above-identified patent and that said Letters Patent is hereby corrected as shown below:

In the Claims

Claim 17, Lines 1-7:
"A chromatography column clamp arranged:
to receive two chromatography columns between a first
compression seal and a movable compression seal; and
to press said two chromatography columns on opposite
sides of a compression seal coupler by urging the
movable compression seal toward the first compression seal."

Should be changed to:
-- A chromatography column clamp arranged:
to receive first and second chromatography columns between a first compression seal and a movable compression seal; and
to press said first and second chromatography columns on opposite sides of a compression seal coupler by urging the movable compression seal toward the first compression seal, wherein
the compression seal coupler retains the second chromatography column in contact with the movable compression seal when the first chromatography column is not pressed against the compression seal coupler. --

Claim 20, Lines 23-30:
"A method of clamping two chromatography columns
in series, the method comprising:
receiving two chromatography columns between a first
compression seal and a movable compression seal; and
pressing said two chromatography columns on opposite
sides of a compression seal coupler by urging
the movable compression seal toward the first compression
seal."

Signed and Sealed this
Seventh Day of April, 2020

Andrei Iancu
*Director of the United States Patent and Trademark Office*

CERTIFICATE OF CORRECTION (continued)
U.S. Pat. No. 10,422,777 B1

Should be replaced with:
-- A method of clamping two chromatography columns in series, the method comprising:
   receiving a first chromatography column between a first compression seal and a movable compression seal,
   receiving a second chromatography column between the first compression seal and a movable compression seal, wherein the second chromatography column is retained in contact with the movable compression seal by a compression seal coupler when the first chromatography column is not pressed against the first compression seal; and
   pressing said first and second chromatography columns on opposite side of the compression seal coupler by urging the movable compression seal toward the first compression seal. --